United States Patent [19]

Vanstone

[11] 4,000,186
[45] Dec. 28, 1976

[54] ERYTHRODIOL DERIVATIVES

[75] Inventor: Anthony Edward Vanstone, Whitton, England

[73] Assignee: Biorex Laboratories, Limited, London, England

[22] Filed: Nov. 7, 1974

[21] Appl. No.: 521,943

[30] Foreign Application Priority Data

Nov. 7, 1973 United Kingdom ............ 51599/73

[52] U.S. Cl. .......................... 260/485 G; 260/410; 260/429.9; 260/448 R; 260/468 K; 260/489; 424/287; 424/289; 424/305; 424/311; 424/312; 424/313

[51] Int. Cl.² ................. C07C 69/16; C07C 69/28; C07C 69/40; C07C 69/60

[58] Field of Search ......... 260/485 G, 448 R, 429.9

[56] References Cited

UNITED STATES PATENTS 3,732,202   5/1973   Jewers et al. ................. 260/485 L

*Primary Examiner*—Jane S. Myers
*Attorney, Agent, or Firm*—Wenderoth, Lind & Ponack

[57] ABSTRACT

The present invention is concerned with new derivatives of erythrodiol of the general formula:

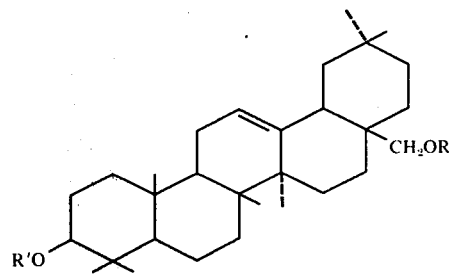

wherein R' is a hydrogen atom or an acyl radical derived from a mono- or polycarboxylic acid and R is a radical derived from a monocarboxylic acid containing 3 or more carbon atoms or from a polycarboxylic acid, any carboxylic acid groups therein being in the free form or in the salt form.

5 Claims, No Drawings

ERYTHRODIOL DERIVATIVES

BACKGROUND OF THE INVENTION

Erythrodiol and certain simple derivatives are known compounds but none of them show remarkable pharmacological properties. In an endeavour to provide new and active anti-inflammatory compounds, I have now found a group of derivatives of erythrodiol which show an especially good activity.

SUMMARY OF THE INVENTION

The new compounds according to the present invention have the general formula:

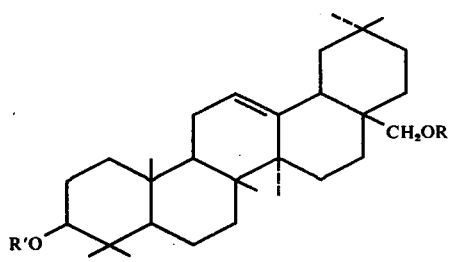

(I)

wherein R is a hydrogen atom or a radical derived from a monocarboxylic acid containing three or more carbon atoms or from a polycarboxylic acid and R' is a hydrogen atom or an acyl radical derived from a mono- or polycarboxylic acid, with the proviso that R and R' are not both hydrogen atoms, any carboxylic acid groups therein being in the free form or in the salt form.

DETAILED DESCRIPTION OF THE INVENTION

Examples of acids with which the hydroxyl groups of the parent erythrodiol may be esterified are preferably mono- and polycarboxylic acids containing up to 20 carbon atoms and preferably containing up to 10 carbon atoms, such as acetic acid, propionic acid, butyric acid, malonic acid, maleic acid, lauric acid, stearic acid, succinic acid, glutaric acid and cyclohexane-dicarboxylic acids.

The new compounds according to the present invention have valuable anti-inflammatory properties and can be administered orally, enterally or parenterally for the treatment of inflammatory conditions.

In order to prepare the new compounds (I), erythrodiol is reacted with a reactive derivative of an appropriate carboxylic acid, for example an acid halide or anhydride. The reaction can be carried out in an inert solvent, pyridine being preferred.

When R and/or R' contains a free carboxylic group, then the product can be reacted with an appropriate non-toxic inorganic or organic basic compound, for example, a basic alkali metal or alkaline earth metal compound or a non-toxic organic amine, such as sodium, potassium, calcium, magnesium, aluminium or zinc hydroxide or carbonate or mono-, di- or trialkylamines. This reaction is preferably carried out in an inert solvent in which the salt is insoluble or only sparingly soluble.

The following Examples are given for the purpose of illustrating the present invention:

EXAMPLE 1

13 g. erythrodiol and 12 g. succinic anhydride in 100 ml. pyridine were heated under reflux for 5 hours, whereafter thin layer chromatography showed the reaction to be complete. The reaction mixture was cooled and poured into ice water containing excess hydrochloric acid and extracted with chloroform. The organic extract was washed with dilute hydrochloric acid and then with water and dried over anhydrous sodium sulphate. The solvent was then removed to give 18 g. of a white foam of erythrodiol dihemisuccinate which could not be crystallised. This crude material was dissolved in 100 ml. of warm ethanol and an aqueous solution of 20% sodium hydroxide was added dropwise to the warm solution until a pH of 8 was reached. Water had to be added from time to time in order to maintain a clear solution. The warm solution was then filtered and an equal volume of acetone was added. Crystals separated out on cooling. They were filtered off, washed with acetone and dried in vacuo at 100° C. 11.5 g. of material were obtained which was recrystallised from aqueous ethanol to give 9.6 g. of the disodium salt of erythrodiol dihemisuccinate which showed no impurities by thin layer chromatography. The product had a melting point of >340° C.; $[\alpha]_D^{26} = +40.6°$ (c. = 1% in methanol/0.2% aqueous sodium carbonate solution (1:1)).

Partial hydrolysis of this disodium salt with an aqueous methanolic solution of sodium carbonate, followed by acidification and working up gave erythrodiol 3-monohemisuccinate, which had a melting point of 270° – 272° C.; $[\alpha]_D^{24} = 69.2 \pm 2°$ (c. = 1% in chloroform/methanol (1:1)).

EXAMPLE 2

17.8 g. erythrodiol, 4.0 g. succinic anhydride and 25 ml. anhydrous pyridine were heated under reflux for 5 hours and then left at ambient temperature overnight. The reaction mixture was then diluted with 150 ml. acetone, poured into ice water containing an excess of hydrochloric acid and the solid material filtered off, washed with distilled water until neutral and dried in a vacuum at 100° C. There were obtained 20.35 g. erythrodiol 28-monohemisuccinate. This was repeatedly recrystallised from dichloromethane/methanol to give 6.8 g. of product with a purity of more than 99% by thin layer and gas chromatography. The product had a melting point of 266° – 267° C.; $[\alpha]_D^{24} = +55.6° \pm 1°$ (c. = 1% in chloroform/methanol (1:1)).

EXAMPLE 3

15 g. erythrodiol, 5.5 g. cis.-cyclohexane-1,2-dicarboxylic acid anhydride and 30 ml. pyridine were refluxed for 3 hours, whereafter the reaction mixture was diluted with 40 ml. acetone and poured into excess ice and hydrochloric acid, while stirring. The resultant gum was extracted with dichloromethane and the extract was washed neutral with water and dried over anhydrous sodium sulphate. The organic layer was decanted off, 200 ml. methanol were added thereto and the mixture was then concentrated to 150 ml. Scratching the vessel with a glass rod initiated crystallisation. Two main crops of crystals, each of 10 g., were obtained. These crystals were recrystallised from a mixture of 150 ml. dichloromethane and 250 ml. methanol. There was thus obtained pure erythrodiol 28-mono-cis-cyclohexane-dicarboxylate, which had a melting point of 282° – 284° C.; $[\alpha]_D^{23} = + 47.5° \pm 1°$ (c. = 1% in chloroform).

EXAMPLE 4 a. A mixture of 10 g. erythrodiol diacetate, 6 g. potassium carbonate and 750 ml. methanol was stirred at 40° C. for 5 hours. After this time, complete solution had been obtained. The reaction mixture was acidified with 70 ml. 2N hydrochloric acid and diluted with 400 ml. water. The precipitated solid was filtered off, extracted with dichloromethane and the extract then washed with water until the washings were neutral and then dried over anhydrous sodium sulphate. The dried organic extract was filtered, diluted with methanol and concentrated to 100 ml., 8.2. g. of a crystalline product being obtained upon cooling in three crops. Recrystallisation of the first crop from ethyl acetate gave 1.7 g. of 99% pure erythrodiol-3-monoacetate, which had a melting point of 234° – 236° C.; $[\alpha]_D^{23.4} = + 65.7°$ (c. = 1% in chloroform).

b. 3 g. erythrodiol-3-monoacetate, 1.2 g. cis-cyclohexane-1,2-dicarboxylic acid anhydride and 5 ml. pyridine were refluxed for 7 hours. The reaction mixture was cooled, diluted with 40 ml. acetone and poured into excess ice water and hydrochloric acid, while stirring rapidly. The precipitated solid was filtered off, washed with water until the washings were neutral and then dried in a vacuum oven at 90° C., 3.3 g. of crude product thereby being obtained. 2.3 g. of this crude product were recrystallised from ethyl acetate/petroleum ether (b.p. 60° – 80° C.) to give a first crop of 1.8 g. pure erythrodiol 3β-acetate 28-monohemi-cis-cyclohexane-1,2-dicarboxylate, which had a melting point of 162° – 164° C.; $[\alpha]_D^{26} = + 46° \pm 0.5°$ (c. = 1% in chloroform).

EXAMPLE 5

5 g. of the disodium salt of erythrodiol dihemisuccinate (see Example 1) were dissolved in 100 ml. aqueous ethanol and the resultant solution was acidified with dilute hydrochloric acid. The reaction mixture was extracted with dichloromethane and the organic extract washed with water and dried over anhydrous sodium sulphate. The solvent was removed to leave 4.6 g. of white foam which was dissolved in methanol/dichloromethane and treated with an excess of ethereal diazomethane. After standing at ambient temperature for 1 hour, the reaction mixture was evaporated to give 5 g. of a pale yellow oil. This was crystallised with difficulty, using methanol. There was thus obtained 3β,28-di-(β-carbomethoxy-propionyl)-erythrodiol, which had a melting point of 62° – 63° C.; $[\alpha]_D^{22} = + 43.9°$ (c. = 1% in chloroform).

EXAMPLE 6

3 g. erythrodiol, 2.5 g. propionic anhydride and 5 ml. anhydrous pyridine were refluxed on an oil bath for 3 hours and then left overnight at ambient temperature. The reaction mixture was then refluxed again for 3 hours, poured into excess ice water and hydrochloric acid, extracted with dichloromethane and the extract washed with dilute hydrochloric acid and distilled water, dried over anhydrous sodium sulphate and evaporated to dryness. 4.6 g. of a yellow oil were obtained. This was crystallised twice from methanol to give 2.5 g. of white, crystalline erythrodiol 3β,28-dipropionate, which had a melting point of 165° – 166° C.; $[\alpha]_D^{26} = + 62.8° \pm 1°$ (c. = 1% in chloroform).

Erythrodiol and lauroyl chloride were reacted in a similar manner in pyridine to give erythrodiol dilaurate, which had a melting point of 50° – 51° C.; $[\alpha]_D^{23} = + 40.8° \pm 1°$ (c. = 1% in chloroform).

The present invention also includes within its scope pharmaceutical compositions containing at least one of the new compounds of general formula (I) in admixture with a solid or liquid pharmaceutical carrier, which can be administered orally or parenterally.

Solid compositions for oral administration include compressed tablets, pills, dispersible powders and granules. In such solid compositions, one of the new esters is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents, and sweetening and flavouring agents.

The compositions according to the present invention, for oral administration, include capsules of absorbable material, such as gelatine, containing one of the new derivatives, with or without the addition of diluents or excipients.

Preparations according to the present invention for parenteral administration include sterile aqueous or non-aqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilised, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The percentage of active material in the compositions of the present invention may be varied, it being necessary that it should constitute a proportion such that a suitable dosage for the desired therapeutic effect shall be obtained. In general, the preparations of the present invention should be administered orally or parenterally to humans to give 10 to 1000 mg., preferably 50 – 500 mg. of active substance per day.

The following Examples illustrate pharmaceutical compositions according to the present invention:

EXAMPLE 7

| | |
|---|---|
| 250 mg. tablets are prepared containing:- | |
| erythrodiol dihemisuccinate disodium salt | 50 mg. |
| starch | 100 mg. |
| lactose | 95 mg. |
| magnesium stearate | 5 mg. |

EXAMPLE 8

| 400 mg. tablets are prepared containing:- | |
|---|---|
| erythrodiol 28-monohemisuccinate | 100 mg. |
| starch | 130 mg. |
| lactose | 160 mg. |
| magnesium stearate | 10 mg. |

The compositions according to Examples 7 and 8 are intended for oral administration to humans for the treatment of inflammatory conditions of the gastro-intestinal tract.

I claim:

1. A compound selected from the group consisting of compounds of the formula

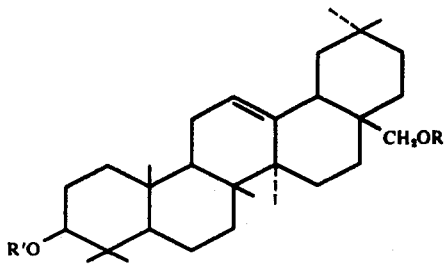

wherein R is hydrogen or an acyl radical derived from a polycarboxylic acid selected from the group consisting of malonic acid, maleic acid, succinic acid and glutaric acid, and R' is hydrogen or an acyl radical derived from a polycarboxylic acid selected from the group consisting of malonic acid, maleic acid, succinic acid and glutaric acid, with the proviso that R and R' are not both hydrogen atoms, and non-toxic salts of said compounds.

2. The compound according to claim 1, which is erythrodiol dihemisuccinate.

3. The compound according to claim 1, which is the disodium salt of erythrodiol dihemisuccinate.

4. The compound according to claim 1, which is erythrodiol 28-monohemisuccinate.

5. The compound according to claim 1, which is erythrodiol 3-monohemisuccinate.

* * * * *